United States Patent
Jay (10) Patent No.: US 8,393,330 B2
(45) Date of Patent: *Mar. 12, 2013

(54) HAIR TREATMENT SYSTEM AND METHOD

(76) Inventor: Harvey H. Jay, Scarsdale, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/531,982

(22) Filed: Jun. 25, 2012

(65) Prior Publication Data

US 2012/0265182 A1    Oct. 18, 2012

Related U.S. Application Data

(63) Continuation of application No. 13/066,788, filed on Apr. 25, 2011, now Pat. No. 8,286,641, which is a continuation of application No. 10/647,948, filed on Aug. 26, 2003, now Pat. No. 7,931,028.

(51) Int. Cl.
A61B 19/00    (2006.01)

(52) U.S. Cl. ............... 128/898; 606/9; 606/133; 607/88

(58) Field of Classification Search ............ 606/3, 9–13, 606/131, 133; 607/88–91; 128/898
See application file for complete search history.

(56) References Cited

U.S. PATENT DOCUMENTS

| | | |
|---|---|---|
| 3,713,453 A | 1/1973 | Chiaro et al. |
| 4,608,978 A | 9/1986 | Rohr |
| 4,819,669 A | 4/1989 | Politzer |
| 4,882,598 A | 11/1989 | Wulf |
| 5,282,842 A | 2/1994 | Changaris |
| 5,374,825 A | 12/1994 | Doty et al. |
| 5,425,728 A | 6/1995 | Tankovich |
| 5,533,266 A | 7/1996 | Kelman |
| 5,595,568 A | 1/1997 | Anderson et al. |
| 5,606,798 A | 3/1997 | Kelman |
| 5,683,380 A | 11/1997 | Eckhouse et al. |
| 5,707,403 A | 1/1998 | Grove et al. |
| 5,735,844 A | 4/1998 | Anderson et al. |
| 5,849,029 A | 12/1998 | Eckhouse et al. |
| 5,879,346 A * | 3/1999 | Waldman et al. ............... 606/9 |
| 5,885,273 A | 3/1999 | Eckhouse et al. |
| 5,895,568 A | 4/1999 | Koltunov |
| 5,916,211 A | 6/1999 | Quon et al. |
| 5,993,440 A | 11/1999 | Ghassemi |
| 6,017,360 A | 1/2000 | Chubb et al. |
| 6,027,495 A | 2/2000 | Miller |
| 6,050,990 A | 4/2000 | Tankovich et al. |
| 6,063,076 A | 5/2000 | Mehl, Sr. et al. |
| 6,152,917 A | 11/2000 | Tankovich |
| 6,162,211 A | 12/2000 | Tankovich et al. |
| 6,162,212 A | 12/2000 | Kreindel et al. |
| 6,171,302 B1 | 1/2001 | Talpalriu et al. |
| 6,174,325 B1 | 1/2001 | Eckhouse et al. |
| 6,187,001 B1 | 2/2001 | Azar et al. |
| 6,228,074 B1 | 5/2001 | Almeida |
| 6,235,016 B1 | 5/2001 | Stewart |

(Continued)

FOREIGN PATENT DOCUMENTS

JP    2001-029124    2/2001

OTHER PUBLICATIONS

Philips Lumea, Model SC2001/01, Product Manual, pp. 1-65, date unknown.

(Continued)

*Primary Examiner* — Ahmed Farah
(74) *Attorney, Agent, or Firm* — Uradnik Law Firm PC (57) ABSTRACT

A hand held device generates a predetermined number of pulses of electromagnetic radiation having a predetermined electromagnetic spectrum, a predetermined duration, a predetermined inter-pulse interval, and a predetermined total energy. The pulse sequence is delivered to a skin surface to reduce or eliminate Xray or ultraviolet radiation damage to the skin surface.

13 Claims, 3 Drawing Sheets

U.S. PATENT DOCUMENTS

| | | | |
|---|---|---|---|
| 6,267,771 | B1 | 7/2001 | Tankovich et al. |
| 6,273,883 | B1 | 8/2001 | Furumoto |
| 6,280,438 | B1 | 8/2001 | Eckhouse et al. |
| 6,306,160 | B1 | 10/2001 | Nidetzky |
| 6,348,694 | B1 | 2/2002 | Gershteyn et al. |
| 6,383,176 | B1 | 5/2002 | Connors et al. |
| 6,387,089 | B1 | 5/2002 | Kreindel et al. |
| 6,406,474 | B1 | 6/2002 | Neuberger et al. |
| 6,452,188 | B1 | 9/2002 | Chubb |
| 6,514,243 | B1 | 2/2003 | Eckhouse et al. |
| 6,533,775 | B1 | 3/2003 | Rizoiu |
| 6,595,986 | B2 | 7/2003 | Almeida |
| 6,602,275 | B1 | 8/2003 | Sullivan |
| 6,610,052 | B2 | 8/2003 | Furumoto |
| 6,663,659 | B2 | 12/2003 | McDaniel |
| 6,676,665 | B2 | 1/2004 | Foley et al. |
| 6,714,293 | B2 | 3/2004 | Goto et al. |
| 6,730,113 | B2 | 5/2004 | Eckhardt et al. |
| 6,824,542 | B2 | 11/2004 | Jay |
| 6,828,576 | B2 | 12/2004 | Spivak |
| 6,861,658 | B2 | 3/2005 | Fiset |
| 6,878,144 | B2 | 4/2005 | Altshuler et al. |
| 6,916,316 | B2 * | 7/2005 | Jay .................................... 606/9 |
| 7,044,959 | B2 | 5/2006 | Anderson et al. |
| 7,108,690 | B1 | 9/2006 | Lefki et al. |
| 7,175,617 | B2 * | 2/2007 | Jay .................................... 606/9 |
| 7,201,764 | B2 | 4/2007 | Pearl et al. |
| 7,217,267 | B2 | 5/2007 | Jay |
| 7,291,141 | B2 * | 11/2007 | Jay .................................... 606/9 |
| 7,553,308 | B2 * | 6/2009 | Jay .................................... 606/9 |
| 7,699,058 | B1 | 4/2010 | Jay |
| 7,931,028 | B2 | 4/2011 | Jay |
| 2002/0016587 | A1 | 2/2002 | Furumoto |
| 2003/0011786 | A1 | 1/2003 | Levy et al. |
| 2003/0055414 | A1 | 3/2003 | Altshuler et al. |
| 2003/0065314 | A1 | 4/2003 | Altshuler et al. |
| 2003/0167033 | A1 | 9/2003 | Chen et al. |
| 2003/0216795 | A1 | 11/2003 | Harth et al. |
| 2004/0024390 | A1 | 2/2004 | Furumoto |
| 2004/0034319 | A1 | 2/2004 | Anderson et al. |
| 2004/0147985 | A1 | 7/2004 | MacFarland et al. |
| 2004/0230258 | A1 | 11/2004 | Altshuler et al. |
| 2004/0230260 | A1 | 11/2004 | MacFarland et al. |
| 2005/0177139 | A1 | 8/2005 | Yamazaki et al. |
| 2006/0142741 | A1 | 6/2006 | Jay |
| 2006/0173447 | A1 | 8/2006 | Jay |
| 2006/0178659 | A1 | 8/2006 | Van Hal et al. |
| 2011/0208272 | A1 | 8/2011 | Jay |

OTHER PUBLICATIONS

Remington iLight Pro, Model IPL6000, Use and Care Guide, pp. 1-44, 2011.
TRIA, Instructions for Use, pp. 1-60, 2007.
ESPIL BSL-10, User Guide, pp. 1-24, date unknown.
Philips SatinLux photo-epilator with IPL technology, Model SC2000/00, product leaflet, 2 pages, Feb. 12, 2011.
TOWN, iPulse Applications Training Manual, Cyden Limited, Mar. 2008, pp. 1-43.
Home Skinovations User Manual, Silk'n Instructions for Use, Home Skinovations Ltd., Feb. 2008, pp. 1-24.
BellaLite by Silk'n, Instructions for Use, Home Skinovations Ltd., Apr. 2009, pp. 1-24.
Kist, et al., Effects on Markers of Apoptosis After Intense Pulsed Light Treatment of Photo Damaged Skin, American Society for Laser Medicine and Surgery Abstracts, Apr. 12, 2006, Abstract No. 26.
Decraene, et al., A Low UVB Dose, with the Potential to Trigger a Protective p53-Dependent Gene Program, Increases the Resilience of Keratinocytes against Future UVB Insults, The Journal of Investigative Dermatology, Nov. 2005, vol. 125, No. 5, pp. 1026-1031.
Halliday, Activation of Molecular Adaptation to Sunlight—A New Approach to Photoprotection, The Society for Investigative Dermatology, Inc., No. 125, pp. xviii-xix, Nov. 5, 2005.
Fitzpatrick's Dermatology in General Medicine, Sixth Edition, Freedberg, et al., Editors, vol. 2, pp. 2350-2352, McGraw-Hill, Medical Publishing Division.
Shen, et al., Modulation of IL-10, IL-12, and IFN-gamma in the epidermis of hairless mice by UVA (320-400 nm) and UVB (280-320 nm) radiation, Journal of Investigative Dermatology, 1999, vol. 113, No. 6, pp. 1059-1064 (Abstract).
Reeve, et al., Ultraviolet A Radiation (320-400 nm) Protects Hairless Mice from Immunosuppression Induced by Ultraviolet B Radiation (280-320 nm) or Cis-Urocanic Acid, International Archives of Allergy and Immunology, 1998, vol. 115, Issue 4, p. 316 (Abstract).
Reeve, et al., Interferon-gamma is involved in photoimmunoprotection by UVA (320-400 nm) radiation in mice, Journal of Investigative Dermatology, 1999, vol. 112, No. 6, pp. 945-950 (Abstract).
Bech-Thomsen, et al., Pretreatment with long-wave ultraviolet light inhibits ultraviolet-induced skin tumor development in hairless mice, Archives of Dermatology, 1988, vol. 124, pp. 1215-1218 (Abstract).
Forbes, et al., Experimental ultraviolet photocarcinogenesis: wavelength interactions and time-dose relationships, National Cancer Institute Monogram, 1978, vol. 50, pp. 31-38 (Abstract).
Courtois, et al., Early Ultraviolet B-Induced G1 Arrest and Suppression of the Malignant Phenotype by Wild-Type p53 in Human Squamous Cell Carcinoma Cells, Experimental Cell Research, 1997, vol. 233, Issue 1, pp. 135-144 (Abstract).
Garssen, et al., UVA exposure affects UVB and cis-urocanic acid-induced systemic suppression of immune resposnes in Lissteria monocytogenes-infected Balb/c mice, Photochemistry and Photobiology, 2001, vol. 73, No. 4, pp. 432-438 (Abstract).
Deland, et al., Treatment of Radiation-Induced Dermatitis With Light-Emitting Diode (LED) Photomodulation, Lasers in Surgery and Medicine, 2007, vol. 39, pp. 164-168, Wiley-Liss, Inc.
Latonen, et al., UV-radiation induces dose-dependent regulation of p53 response and modulates p53-HDM2 interaction in human fibroblasts, Oncogene, 2001, vol. 20, pp. 6784-6793, Nature Publishing Group.
Verschooten, et al., Invited Review: New Strategies of Photoprotection, Photochemistry and Photobiology, 2006, vol. 82, pp. 1016-1023, American Society for Photobiology.
Li, et al., p53-Dependent DNA repair and apoptosis respond differently to high- and low-dose ultraviolet radiation, British Journal of Dermatology, 1998, vol. 139, pp. 3-10, British Association of Dermatologists.
Menezes, et al., Non-Coherent Near Infrared Radiation Protects Normal Human Dermal Fibrolasts from Solar Ultraviolet Toxicity, The Journal of Investigative Dermatology, 1998, vol. 111, pp. 629-633, The Society for Investigative Dermatology, Inc.
Frank, et al., Infrared radiation induces the p53 signaling pathway: role in infrared prevention of ultraviolet B toxicity, Experimental Dermatology, 2005, vol. 15, pp. 130-137.
Barton, et al., Cooperative Phenomena in Two-pulse, Two-color Laser Photocoagulation of Cutaneous Blood Vessels, Photochemistry and Photobiology, 2001, vol. 73, No. 6, pp. 642-650, American Society for Photobiology.
Maeda, et al., Nucleotide Excision Repair Genes are Upregulated by Low-Dose Artificial Ultraviolet B: Evidence of a Photoprotective SOS Response?, Journal of Investigative Dermatology, 2001, vol. 117, pp. 1490-1497, The Society for Investigative Dermatology, Inc.
Anderson, et al., U.S. Appl. No. 60/363,871, filed Mar. 12, 2002.
File History for U.S. Appl. No. 10/291,086, now US Patent No. 6,824,542 (Jay).
Notice of Allowance and Fees Due, including the Examiner's Statement of Reasons for Allowance, for U.S. Appl. No. 10/291,086, now US Patent No. 6,824,542 (Jay).
"Effects of Fluence and Pulse Duration for Flashlamp Exposure on Hair Follicles," presented at the 21st Annual Meeting for the American Society for Laser Medicine & Surgery, Apr. 2001 ("Manstein").

* cited by examiner

HAIR TREATMENT SYSTEM AND METHOD

CROSS-REFERENCE TO RELATED APPLICATION

This application is a continuation of application Ser. No. 13/066,788 filed Apr. 25, 2011 as a continuation of application Ser. No. 10/647,948 filed Aug. 26, 2003, now U.S. Pat. No. 7,931,028.

BACKGROUND OF THE INVENTION

This invention relates generally to a process for treating the skin with light, i.e., electromagnetic radiation in the visible and infrared portions of the electromagnetic spectrum.

Exposure to Xrays and/or Ultraviolet (UV) light can produce damage to skin and body tissues. This damage can produce immediate, short term or long term changes. These changes can be temporary or permanent. Benign skin changes can range from temporary irritation such as seen in radiation burns or sun burns, or can be more delayed such as radiation dermatitis or chronic sun damage (poikiloderma).

Malignant changes can include pre-cancerous lesions such as Actinic Keratoses or leukoplakia or cancerous changes such as squamous cell carcinoma, or basal cell carcinoma, or malignant melanoma. These changes frequently occur in the exposed tissue, but they also occur in non-exposed areas. Among the three most common skin cancers (basal cell carcinoma, squamous cell carcinoma, and melanoma), melanoma has been reported to be the most common in non-sun exposed areas, while it is the least common overall of the three skin cancers.

Procedures for preventing damage from Xrays and UV light include: avoiding exposure, and using mechanical or chemical screens to block the energy waves, as well as oral or topical products such as antioxidants, or retinoids to prevent or repair the damage before or after damage has occurred. Topical or oral chemotherapy has also been used to reverse or prevent progressive damage, precancerous or cancerous changes. Surgery with scalpels, surgical instruments or with cutting lasers has been used to remove or ameliorate damaged, precancerous or cancerous areas.

Xrays have also been used to selectively target cancers. By delivering Xray energy to specific sites, those sites may selectively be damaged or destroyed. Even though the long-term side effects may include scarring and/or precancer and/or cancer, the beneficial shorter term clearing of the undesirable tissue may outweigh the longer-term risks. These benefits are especially valuable in the elderly patient.

Light in the visible and/or infrared spectrum has been applied to skin surfaces for purposes of treating blood vessels, pigmentary changes, and irregular surface topography of the skin (elevations and/or depressions and/or scarring). The light is applied either alone or in combination with photosensitizing agents and specifically targets chromophores such as the hemoglobin in blood, melanin in skin, or porphyrin photosensitizers that accumulate in target tissue.

Photodynamic therapy (also called PDT, photoradiation therapy, phototherapy, or photochemotherapy) is a treatment for some types of cancer. It is based on the discovery that certain chemicals known as photosensitizing agents can kill one-celled organisms when the organisms are exposed to a particular type of light. PDT destroys cancer cells through the use of light in combination with a photosensitizing agent.

In PDT, the photosensitizing agent is injected into the bloodstream and absorbed by cells all over the body. Alternatively, the photosensitizing agent may be applied topically for treating precancerous and cancerous skin. The agent accumulates more in cancer cells than it does in normal cells. When the treated cancer cells are exposed to light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The light may have a wavelength between 650-800 nm for tissue penetration purposes.

The photosensitizer used in photodynamic therapy should be partially hydrophilic for injection and delivery purposes and partially lipophilic for cell uptake purposes. Porphyrins are typically used as photosensitizers. Polarity and partition coefficient of these compounds can be altered by attaching polar residues (such as amino acids, sugars, nucleosides) onto the fundamentally hydrophobic porphyrin ring.

In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity. Researchers are also looking at different laser light types, photosensitizers that can be applied to the skin to treat superficial skin cancers, and new photosensitizing agents that may increase the effectiveness of PDT against cancers that are located further below the skin or inside an organ.

Researchers have investigated the effect of visible light treatments on sun-damaged skin. The investigation applied light in two periorbital treatments six weeks apart. In each session, the light had a wavelength of 590-1200 nm and was applied in two pulses each of 4.5 msec duration, with an interpulse interval of 10 msec and a total applied energy of 42 $J/cm^2$. The researchers found an increase in cancer-destroying enzymes MMP-I, MMP-II, TIMP-II, Caspase III. The investigation uncovered a localized increased expression of protein in the fibroblasts after the treatment. The researchers suggested that the application of electromagnetic radiation to sun-damaged skin might reduce the chances of skin cancer formation and theorized that the light treatment stimulates dermal fibroblasts to increases the production of matrix metaloproteases, their inhibitors, and markers of apoptosis.

OBJECTS OF THE INVENTION

An object of the present invention is to provide a method for treating skin to promote and/or protect the health of the skin and underlying tissues.

It is a more specific object of the present invention to provide a method for treating skin as a prophylactic measure.

An even more specific object of the present invention is to provide such a treatment method that reduces or inhibits skin tissue damage that might otherwise accrue owing to Xray or ultraviolet light exposure.

It is further object of the present invention to provide such a treatment method that is safe for home use.

It is a related object of the invention to provide such a treatment method that is easy to use.

A further related object of the present invention is to provide such a treatment method that can result in smooth healthy skin and underlying tissue layers.

These and other objects of the present invention will be apparent from the drawings and descriptions herein. It is to be understood that each object of the invention is achieved by at least one embodiment of the invention. It is not necessarily the case that any embodiment achieves all of the objects of the invention.

SUMMARY OF THE INVENTION

The present invention contemplates the use of electromagnetic energy to prevent, or treat damage from Xray or UV light. The light treatment of a skin surface is effectuated in the absence of visually detecting any Xray or ultraviolet radiation damage to the skin surface. Thus, the present invention is directed to the preclinical treatment of skin as a prophylactic measure against potential Xray or ultraviolet radiation damage.

Visible and/or infrared light energy applied to a skin surface pursuant to the present invention is absorbed by melanin in the epidermis and hemoglobin in the capillaries and blood vessels of the dermis. The absorption of light (visible and/or infrared) increases the local temperature in the tissues containing the chromophores, such as the blood vessel cell walls and keratinocytes in the skin. The rise in heat of these structures above a certain level stimulates a healing response and a release of growth factors and other tissue substances. This is done without permanently damaging these structures.

The increase in the temperature of the target tissues is effectuated in addition by energy transfer owing to light scattering. Energy transfer in this case does not arise from light interaction with a chromophore but rather by random light interaction with undetermined other molecular species.

The present invention further contemplates that the light application to a skin surface is undertaken in anticipation of, or during or shortly after, an exposure of the individual to the sun or other source of Xray and ultraviolet radiation. If the application of light precedes potentially dangerous exposure, it is preferred, but not required, that the treatment is as close as possible to the time of exposure. Similarly, if the application of light occurs after potentially dangerous exposure, the delay before skin treatment is preferably, but not necessarily, minimized. The invention finds that intervals of minutes or hours between light treatment and exposure are optimal. The invention recognizes, however, that benefits may be attained even if the intervals between the exposure and the light treatment are on the order of days.

Nevertheless, where several treatment sessions are used, some or all of those treatments may be scheduled at times substantially removed from the time of exposure to Xray or UV radiation. For individuals who are exposed to the sun regularly, it is possible for the light treatments to be done regularly as well. For instance, daily or weekly treatments may be optimal for some individuals.

More specifically, the present invention contemplates delivering, to a skin surface, visible light and/or infrared light with a wavelength of about 400 to about 1200 nm, in particular, either alone or in combination with sound waves, ultrasound waves and/or magnetic waves. A method pursuant to the present invention serves to prevent, reduce, improve, or clear the potential, immediate, chronic and/or long term changes resulting from non-beneficial energy.

Selection of complementary energy settings which may offset the physical, biochemical, or any negative change produced by the undesirable energy—will benefit the patient.

This beneficial energy may be delivered to any area—whether including or excluding the original target area of the undesirable energy. This beneficial energy may be delivered at any time—before, during, or after the undesired energy is delivered or in various combinations thereof.

Where an individual's skin is exposed to deleterious energy at a beach or a tanning salon, it is possible to deliver the prophylactic light energy to the individual's entire skin surface in a small chamber containing the user. The user preferably wears goggles to protect the eyes and may stand in a small enclosed space—a light chamber—during the application of light to the entire skin surface. The light may be applied via a contact device, as described specifically herein with reference to the drawings, and/or via a non-contact apparatus, as discussed below.

Beneficial energy may be delivered in varying combinations and strengths. The protocols for delivering beneficial energy may be standardized based on experience or may be individualized based on analysis of specific exposures and changes induced or produced by undesirable energy exposures.

Means for delivering the desirable energy may include hand-held or larger sized devices. These devices may be located in residential and/or commercial, public and/or private, indoor and/or outdoor settings—and may be used on a prescribed regimen or individualized regimen with or without known exposure to undesirable energy.

In accordance with another feature of the present invention, it is possible to provide the skin with an exogenous chromophore that is absorbed into essentially all the dermal or epidermal cells for purposes of enhancing light absorption. This option is particularly desirable for individuals with skin of low natural melanin content. One such chromophore is porphyrin, that may be applied topically, to facilitate selective absorption by the target skin tissues. It is noted that melanin or precursors of melanin are not generally absorbable into the skin. As indicated above, beneficial effects of light treatment may be achieved by a scattering mechanism instead of absorption, in which case an exogenous chromophore is not necessary.

A skin treatment method in accordance with the present invention comprises applying an effective amount of electromagnetic radiation to a target skin surface to at least partially prevent, reverse, or inhibit damage to the skin caused by exposure of the individual (and not necessarily the target skin surface) to Xray or ultraviolet radiation, such as from the sun. The electromagnetic radiation is applied to the skin surface on at least one occasion prior to, during or after the exposure of the individual to Xray or ultraviolet radiation. It is contemplated that the radiation is applied to the skin surface in the absence of any visible Xray or ultraviolet radiation damage on the skin surface. The radiation is applied as a prophylactic or preventitive measure to obviate any possible Xray or ultraviolet radiation damage that might otherwise occur because of exposure to the sun or other source of Xray or UV radiation.

It is to be noted that the present invention contemplates in part the treatment of skin areas that are not exposed directly to the sun or other source of Xray or UV radiation. Accordingly, skin surfaces that are covered by clothing during an individual's exposure to the sun may be subject to the light treatment of the present invention. Such treatment is based on the fact that melanomas are known to occur in non-exposed areas of an individual's skin. The mechanism for this is not known and may possibly rest on a blood factor.

Pursuant to another feature of the present invention, the applying of the electromagnetic radiation includes (a) generating a predetermined number of pulses of electromagnetic radiation each having a predetermined electromagnetic spectrum, and (b) directing the pulses of electromagnetic radiation towards the skin surface of the individual, who is exposed to Xray or ultraviolet radiation. The pulses have at least one pulse duration and a total energy all predetermined to reduce direct or indirect Xray or ultraviolet radiation damage to the tissues of the skin surface. "Direct" radiation damage refers to skin areas that are exposed to Xray or ultraviolet radiation, whereas "indirect" radiation damage refers to skin areas that are shielded, for instance, by clothing during exposure of the individual to Xray or ultraviolet radiation.

Pursuant to more specific features of the present invention, the number of pulses is greater than one, the pulses have an inter-pulse interval between approximately 1 msec and 500 msec, the total energy is between approximately 0.01 Joule and approximately 200 Joules of energy per square centimeter of the skin surface, and the pulse duration is between about 1 msec and 2 sec.

Even more specifically, the pulse duration is between about 1 msec and 100 msec, whereas the total energy is between approximately 1 Joule and approximately 90 Joules of energy per square centimeter of the skin surface.

In one particular embodiment of the method in accordance with the present invention, the number of pulses is two, the pulse duration is about 5.8 msec, the interpulse interval is approximately 20 msec, and the total energy applied is between about 20 Joules per square centimeter of the skin surface and about 90 Joules per square centimeter of the skin surface.

In another particular embodiment of the method in accordance with the present invention, the number of pulses is one, the pulse duration is between about 18 msec and 25 msec, and the total energy applied is between about 20 Joules per square centimeter of the skin surface and about 90 Joules per square centimeter of the skin surface.

Preferably, the electromagnetic radiation of the pulses is incoherent and wherein the spectrum includes wavelengths between about 400 nm and 1200 nm. It is furthermore preferable to apply the light during any given treatment session in pulse packets that are separated by a period that is great in comparison to the interpulse duration(s) of the pulse packets. This inter-packet period may be anywhere from one-tenth of a second to several minutes. Where a hand treatment device is being used, it is convenient to treat an entire skin surface with a first pulse packet during a first pass and then treat the same skin surface with a second pulse packet during a second pass. Where a light chamber is used, the individual may wait as long as a few minutes between successive pulse packets, without incurring any fatigue or boredom.

The use of multiple passes enables each pulse packet to deliver a smaller amount of energy, thus lowering the intensity or the rate that the light energy is applied to the skin surface. Instead of 50 Joules/cm$^2$ delivered in one pass, 20-25 Joules/cm$^2$ are delivered in each of two passes. Further reduction in the applied energy to 1 Joule/cm$^2$ or less is possible, without adversely impacting the effectiveness of the treatment, provided that the number of passes is increased to enable sufficient application of energy. This multiple pass treatment is not only effective to treat the target skin surface but is safer and results in fewer side effects. There is a reduced risk of burning or irritation. The treated individual cannot even sense that the light treatment has occurred. The multiple pass method is particularly effective in treating skin that is tanned or otherwise heavily pigmented. Further advantages of using multiple passes include the manufacture of safer machines at less expense.

It is hypothesized that the effectiveness of multiple passes stems in part from chemical reactions that are induced from the light applied during the first pass. It is possible that light absorbed by melanin, hemoglobin, and other lights-sensitive molecules causes a conformational or chemical change in those molecules that renders the molecules more receptive to additional light absorption, perhaps of light of different wavelengths. Accordingly, broadband light treatment is desirable in the absence of knowing exactly which wavelengths are absorbed at which times by which molecules.

The present invention contemplates that the electromagnetic radiation may applied to the skin surface in different treatment sessions on multiple occasions each in conjunction with a respective exposure of the individual to Xray or ultraviolet radiation. Thus, an individual may apply the radiation to his or her skin prior to, during, and/or after each exposure of the individual to the sun. Where the individual has a regular and continuing exposure to Xray or ultraviolet radiation, the individual may apply the electromagnetic energy to his or her skin with a periodicity corresponding to that of the individual's exposure.

Pursuant to the present invention, each application of the electromagnetic radiation to the skin surface is effectuated within a certain interval of a respective exposure of the individual to Xray or ultraviolet radiation. Preferably, but not necessarily, the application of electromagnetic radiation to a skin surface is within one day or twenty-four hours of the exposure of the individual to Xray or ultraviolet radiation. More preferably, the application of electromagnetic radiation to a skin surface is within twelve hours of the exposure of the individual to Xray or ultraviolet radiation. Most preferably, the application of electromagnetic radiation to a skin surface is within one hour of the exposure of the individual to Xray or ultraviolet radiation. These intervals apply regardless of whether the application of electromagnetic radiation to a skin surface is prior to or after the exposure of the individual to Xray or ultraviolet radiation. In any event, the present invention contemplates the application of light in the visible and/or infrared spectrum to skin that is visibly undamaged by Xray or UV radiation exposure, whether solar or otherwise. The light treatment is therefore a preclinical or prophylactic method.

The electromagnetic radiation applied to the skin surface may have a wavelength absorbable by an endogenous chromophore in tissues along the skin surface. The endogenous chromophore may be melanin and/or hemoglobin. In the case of melanin, the natural melanin content of the skin may be enhanced by topical application of a composition containing, for instance, porphyrin or other chromophore absorbable through the epidermis.

Where the applying of the electromagnetic radiation to the skin surface is carried out on multiple occasions or sessions, at least one of the occasions may be further removed in time than at least another of the occasions from the exposure of the individual to Xray or ultraviolet radiation. This is particularly the case where the multiple applications of electromagnetic radiation are all before or all after the exposure to Xray or ultraviolet radiation. Where there are but two applications of electromagnetic radiation, one before and one after the Xray or UV radiation exposure, those applications may possibly occur at the same time interval before and after the exposure.

The occasions or sessions of electromagnetic radiation application may be regularly spaced in time from one another, for instance, daily or weekly. Successive sessions are typically spaced by at least about a half hour from one another. Preferably, successive sessions are spaced by an inter-session interval of at least several hours.

In accordance with another feature of the present invention, the method comprises the transmission of ultrasound energy into biological tissues along the target skin surface prior to, during, after, or in lieu of applying the electromagnetic radiation to the skin surface. Alternatively or additionally, the method also comprises applying a magnetic field to biological tissues along the skin surface prior to, during, after or in lieu of the applying of the electromagnetic radiation to the skin surface.

Accordingly, a skin treatment method in accordance with the present invention comprises applying an effective amount of mechanical pressure waves to a skin surface to at least partially prevent, reverse, or inhibit damage to the skin caused by exposure to Xray or ultraviolet radiation. The mechanical pressure waves are applied to the skin surface on at least one occasion prior to, during or after the exposure of the individual to Xray or ultraviolet radiation. The application of the mechanical pressure waves to the skin surface is effectuated in the absence of any visible Xray or ultraviolet radiation damage to the skin surface. The mechanical pressure waves may have a sonic or ultrasonic frequency.

Concomitantly, a skin treatment method in accordance with the present invention comprises applying an effective amount of magnetic energy to a skin surface to at least partially prevent, reverse, or inhibit damage to the skin caused by exposure to Xray or ultraviolet radiation. The magnetic energy is applied to the skin surface on at least one occasion prior to, during or after the exposure of the individual to Xray or ultraviolet radiation. The magnetic energy is applied to the skin surface in the absence of any visible Xray or ultraviolet radiation damage to the skin surface. The magnetic energy may be applied in the form of an alternating magnetic field. The frequency of field oscillation may be anywhere from several Hz to several million Hz.

A prophylactic skin treatment method particularly directed to the treatment of ostensibly undamaged or preclinically damaged skin preferably comprises, in accordance with the present invention, (i) generating a predetermined number of pulses of electromagnetic radiation each having a predetermined electromagnetic spectrum, (ii) applying the pulses of electromagnetic radiation to an individual's skin surface, the pulses having at least one predetermined pulse duration, and a predetermined total energy, (iii) exposing the individual to Xray or ultraviolet radiation, and (iv) at least in part owing to the applying of the pulses to the skin surface, reducing or preventing damage to the tissues of the skin surface arising from the exposing of the individual to Xray or ultraviolet radiation. The electromagnetic spectrum may include at least one wavelength absorbable by an endogenous chromophore (e.g., melanin and hemoglobin) in the person's skin tissues.

A device for skin treatment comprises, in accordance with the present invention, a hand-holdable casing, a generator of electromagnetic radiation mounted to the casing, means on the casing for directing radiation from the generator to a skin surface, and an ancillary energy generator mounted to the casing for producing another form of energy for application to the skin surface.

The ancillary energy generator may be an ultrasonic pressure wave device including an electromechanical transducer and an ultrasonic-frequency electrical wave generator.

Where the means for directing electromagnetic radiation to a skin surface includes a flexible applicator member at least partially conformable to a topography of the skin surface, the ultrasonic transducer is in operative contact with the flexible member for transmitting ultrasonic pressure waves to the skin surface through the flexible member. The flexible member may take the form of a fluid-filled pouch.

The ancillary energy generator may include an electromagnet for the application of a magnetic field to the skin tissues.

The pulse parameters, namely, the pulse number, the pulse duration(s), the inter-pulse interval(s), the total energy and the spectral distribution(s), are selected in concert to reduce or prevent Xray- and/or UV-light-induced damage to the treated skin surface. This selection may be made in accordance with (1) a chromophore concentration within the target skin tissues and/or (2) the expected amount (frequency, duration, intensity) of Xray and/or UV light exposure. A consumer device for the application of electromagnetic radiation pulses in accordance with the present invention may be preprogrammed to select the pulse parameters in accordance with user input as to the darkness of the user's skin and the amount of exposure to the sun or other source of Xray and UV radiation. Alternatively, a light applicator device may provide for user selection of pulse parameters. The input of skin tone and exposure levels and/or the selection of pulse parameters may be effectuated via separate actuators such as knobs or via a keyboard or keypad. In the latter case, the user input or selection process may be directed by prompts shown on a display under the control of a microprocessor.

The electromagnetic radiation used in a skin treatment method in accordance with the present invention may be incoherent and produced by a flashlamp or other source of incoherent electromagnetic radiation. Alternatively, the applied radiation may be coherent and produced by a laser source. In the former case the electromagnetic spectrum of the light pulses is a band of wavelengths, while in the latter case, the electromagnetic spectrum of a light pulse delivered at one time is a single wavelength or a set of single wavelengths. In the former case filters may be used to limit the band of transmitted wavelengths, while in the latter case the laser source may be adjustable or tunable for producing wavelengths of different frequencies. The light energy applied may include at least one wavelength absorbable by an endogenous chromophore in skin tissues such as melanin or hemoglobin.

In accordance with the present invention, a user determines the tone or melanin content of a selected skin surface, as well as the quantity and nature of exposure to the sun or other source of Xray and UV radiation. The pulse parameters of the light application are then automatically or partially automatically selected in accordance with the determined skin tone and radiation exposure. Where the user is allowed to select pulse parameter values, there will be an automatically implemented limitation on the selection of parameter values so that the light energy applied will not be dangerous to the health of the target skin.

The method of the present invention contemplates a frequency of light treatment that is consistent with the frequency and intensity of the individual's exposure to the sun or other source of dangerous radiation. For example, a user may apply the pulsed light energy daily where the individual has daily sun exposure. Where the individual goes outdoors only once a week (for example, to shop), the user may apply the pulsed light energy weekly.

Pursuant to the present method, light energy may be applied to an exposed or unexposed skin surface prior to the exposure of the individual to Xray or ultraviolet radiation. If the individual fails to apply light prior to radiation exposure, he or she may apply the light energy after the exposure. For instance, if a user goes to the beach serendipitously, the user may apply light pulses in the evening, after the user returns to his or her place of abode.

The effect of light treatment in accordance with the present invention will depend in part on the individual's genetics as to skin color and on the selected treatment parameters such as total energy, pulse rate, pulse duration, light spectrum, etc., as well as by the particular area on the user's body. The effect of the light treatment will depend in part on the quality and quantity of exposure to the sun or other source of potentially harmful radiation. In any given individual, the amounts of melanin and hemoglobin in facial, underarm, leg tissues, etc., vary.

The method of the present invention may be applied to facial skin, leg skin, arm skin, neck and chest skin, etc., using hand held devices of prior art designs, for instance, with a light source such as a flashlamp, a reflector, one or more lenses, and an application interface such as a skin-contacting crystal. The crystal may function as a cooling element. Alternatively, a separate cooling medium such as a gel may be applied to the skin surface prior to the light application.

It is hypothesized that light administered in accordance with the present invention including wavelengths that are multiples of the 200-400 nm wavelength range of ultraviolet radiation. It is considered that the prophylactic effect of light treatment is largely owing to those wavelengths that bear a harmonic relationship to the wavelengths of the damaging radiation. Thus, light at wavelengths of 800 nm, and 1200 nm are particularly beneficial to obviating the adverse effects of ultraviolet light having a wavelength of 200 or 400 nm. Pursuant to this theory, light is best administered over a range of wavelengths where the ultraviolet radiation occurs in a range of wavelengths including 200-400 nm.

Accordingly, the present invention contemplates the use of a hand held device for generating a predetermined number of pulses of light having a predetermined electromagnetic spectrum and for applying the pulses of light to skin, the pulses having one or more predetermined durations, one or more predetermined inter-pulse intervals (if number of pulses is greater than one), and a predetermined total energy. The device is used to temporarily provide healing impetus to skin. Light pulses applied to a skin surface are expected to have an optimal prophylactic affect up to about twenty-four hours after the application of the light pulses. However, light pulses applied more than twenty-four hours prior to sun (or other) exposure will still have a benefit, although reduced. Where the interval between a light application and a subsequent radiation exposure is more than twenty-four hours, it is recommended that at least one other light application be carried out within twenty four hours after the exposure. Regular treatment of the skin with light pulses will have a beneficial effect even if undertaken without attention to the frequency, times, and nature of potentially harmful radiation exposure. Thus, light treatment may be used generally to promote skin health.

The light treatments may be performed without application of exogenous chromophores for light absorption purposes. Skin treatment is then effectuated through light absorption solely by endogenous chromophores such as melanin and/or via light scattering in the epidermal, dermal and subdermal tissues. Exogenous chromophores may be added for purposes of enhancing the light absorption. This option is particularly appropriate for persons of light skin tone. Porphyrin may be used as an endogenous chromophore, preferably applied via a topical cream or gel.

The inter-pulse interval (where the number of pulses is greater than one) may, in different applications of the invention, be anywhere from 1 millisecond to 2 seconds. Generally, the smaller the inter-pulse interval, the greater the risk of damage to the skin. Thus, the smaller inter-pulse intervals should be used only in professional settings. In home-based embodiments of the invention, the inter-pulse interval of a light treatment is preferably greater than about 20 msec and more preferably greater than 200 msec. An inter-pulse interval of such a magnitude reduces the chances of inadvertent damage to the epidermis. Preferably, the inter-pulse interval is between 200 msec and about 500 msec. An inter-pulse interval of 300 msec is effective.

The total energy applied may be anywhere from 0.01 Joule per square centimeter of treated skin surface to about 200 $J/cm^2$. Generally, the higher energies entail greater risk to skin integrity and should be used only by skilled professionals. For home use, the total energy applied should be lower, preferably between approximately 1 $J/cm^2$ and approximately 100 $J/cm^2$ of the skin surface and more preferably between approximately 5 $J/cm^2$ and approximately 90 $J/cm^2$ of the skin surface. The higher portion of this energy range is appropriate for persons of light skin color. Where the skin color is on the dark side, the upper limit of the total energy applied to a unit of skin surface should be less, for instance, approximately 20 $J/cm^2$.

Generally, it is contemplated that devices used in a method pursuant to the present invention will require a selection of a maximum or total energy to be applied to a skin surface. This requirement typically entails some restriction on the user's freedom in selecting the magnitudes of other pulse parameters. In a simple device, the user may be able to select only one pulse parameter, namely the total energy. Such a device might, for instance, have high, medium and low settings, alternatively designated as light skin, medium tone skin, and dark skin settings. In a more complex device, setting of the total energy applied by a pulse sequence will limit the range of options available to the user in setting the other parameters. For instance, once the user selects the total energy and the pulse duration, the number of pulses is determined, provided that the rate of energy production or intensity is not adjustable. If the intensity is adjustable, the user will have some leeway in selecting both the pulse duration and the number of pulses. In that case, the intensity may be automatically controlled by the light-generating device so that the total energy does not exceed the set value.

The duration of the light bursts or pulses may be as little as 1 millisecond or as great as two seconds. The shortest durations and higher energies are recommended for professionally supervised light treatments only. For ordinary consumers or unskilled users, the pulse duration should be longer, preferably above approximately 5 msec and more preferably between approximately 5 msec and approximately 30 msec.

Pursuant to one embodiment of the present invention, the light of the pulses is incoherent and the spectrum includes wavelengths between about 400 nm and 1200 nm. Longer wavelengths are used for darker skin, for deeper skins and deeper removal. In some embodiments of the invention, the spectrum of the pulses may be limited to wavelengths between about 400 nm and 550 nm. These embodiments will require a more frequent application of the light energy to effectuate skin treatment.

The number of pulses in each pulse sequence or treatment session (as applied to a given skin area) may be between one and ten, while the total duration of a pulse sequence ranges between 1 millisecond and 38 seconds.

As indicated above, the present invention contemplates that some adjustment may be made by the user in the particular operational parameters of the light application device. For instance, a simple hand-held device may have a plurality of settings, for instance, high, medium, and low (light skin, medium skin, dark skin), where one or more of the operational parameters have different pre-established values depending on the setting. Thus, high, medium, and low settings may vary in the number of applied pulses, the pulse duration, the inter-pulse interval, and/or the total energy applied. A user could start with a low setting to see whether the skin is adversely affected in any way and if not, try the next higher setting. Usually, it is preferable to use a lower setting.

It is to be noted that consumer devices may be preprogrammed with automatically operating safety controls that inhibit the user from inadvertently exposing himself or herself to dangerous quantities of light energy. Thus, in a relatively complex consumer product, the user's setting of one parameter at a potentially dangerous value will cause the device either to limit the selectable ranges of one or more other pulse parameters or to automatically adjust pulse parameters to prevent an excessive rate of energy delivery. For instance, the selection of a small inter-pulse interval (with a fixed total energy value) may prevent the user from selecting a short pulse duration and/or a small number of pulses (that would result in a high intensity) or, alternatively, may result in an automatic diminution of the intensity (e.g., via engagement of an intensity-reducing filter).

A device for skin treatment comprises, in accordance with a feature of the present invention, a hand-holdable casing, a light generator mounted to said casing, and an applicator mounted to the casing for applying light from the generator to the skin surface. The applicator includes a flexible member at least partially conformable to the topography of the skin surface. The flexible member may take the form of a fluid-filled pouch or a piece of resilient plastic material. In either event, the applicator is at least partially transparent to the light produced by the generator for application to the skin surface.

The hand-held light treatment device may incorporate a generator of ultrasonic vibrations and/or an electromagnet for enabling the application of ultrasound energy or a magnetic field (preferably oscillating) to a skin surface before, during or after the application of light energy. In the case of ultrasound energy, one or more piezoelectric crystals are disposed in contact with the applicator interface, e.g., a flexible fluid-filled pouch. A wave generator transmits an ultrasonic-frequency electrical signal to the piezoelectric crystal(s) for producing ultrasonic vibrations in skin tissues.

Pursuant to another feature of the present invention, a marker film is applied to a light-treated skin surface to indicate that electromagnetic radiation has been applied to the skin surface. The marker film may include a visually detectable pigment, for instance, zinc oxide, titanium dioxide, or a tinted transparent wash or dye. Where multiple passes are to be made to a skin surface, the first and other non-final passes may leave a transparent or partially transparent film, while the final pass deposits an opaque coating (e.g., zinc oxide or titanium dioxide) that is reflective so as to protect the skin against further inadvertent light exposure. The initial film deposits may be partially reflective to provide some measure of protection against inadvertent overexposure. Alternatively, the marker film may be a visually undetectable composition, exemplarily micronized or microfine zinc oxide. In that case, the light application device is provided with a sensor that detects the marker film and disables or blocks light application to any skin surface already treated with an effective amount of light.

The marker film is preferably applied by the same device that generates the light and directs the light to a skin surface. In that case, the device is provided with a reservoir of the marker composition and an applicator such as a roller, nozzle, or atomizer.

Where several passes of light application are to be made to the skin surface, each may be marked by an indicator composition of a respective tint or color. The marker compositions should be both biocompatible and water soluble for easy removal.

A hair treatment device in accordance with another feature of the present invention the present invention comprises a hand-holdable casing, a generator of electromagnetic radiation mounted to the casing, and at least one optical element mounted to the casing so as to direct electromagnetic radiation produced by the generator in a direction substantially parallel to a skin surface, to impinge on hair fibers protruding from the skin surface. The optical element may take the form of a partially reflective and partially transmissive mirror.

A light treatment device comprises, in accordance with a further feature of the present invention, a hand-holdable casing, and an applicator interface attached to the casing, the interface including a liquid-filled chamber having a flexible skin-contacting surface or panel. A generator of electromagnetic radiation is mounted to the casing, while at least one optical element mounted to the casing directs light from the generator through the liquid in the chamber towards a skin surface in contact with the flexible skin-contacting surface or panel. Preferably, the flexible skin-contacting surface or panel is transparent to the light from the generator.

A light treatment method in accordance with an additional feature of the present invention comprises generating light of a selected spectral composition, dividing the light into at least two bundles of light rays of substantially mutually exclusive wavelength ranges, and directing at least one of the bundles of light rays towards a skin surface.

Where the one bundle of light rays is directed into the skin surface, the other bundle may be directed substantially parallel to the skin surface to impinge on hairs protruding from the skin surface. The one bundle may include wavelengths in a range below approximately 750 nm, while the other bundle includes wavelengths in a range above approximately 750 nm. Goggles for wear during light treatment in accordance with this feature of the invention may be provided with lenses substantially opaque to light rays of the infrared bundle (750 nm and above) and at most partially transparent to light rays of the other bundle. For example, the goggles may be opaque to all visible wavelengths except a narrow band of wavelengths that are not included in the bundle of wavelengths below 750 nm. If the goggles are completely transparent to this narrow wavelength band, the band is filtered out of the visible light bundle. An indicator light such as an LED may be provided that emits light in the narrow band to provide a signal to the user that dangerous radiation is being produced. Alternatively, the goggles may be at most partially transparent to the narrow wavelength band. In this case, the goggles transmit enough light of the narrow band to enable visual detection but not enough to damage the eye.

A hair treatment method comprises, in accordance with yet another feature of the present invention, generating light of a selected spectral composition, applying a dye to hair along a skin surface, and thereafter directing the generated light towards the dyed hair along the skin surface. This method is of particular for the removal of hair that is white or very light colored. Preferably, the dye is applied to a selected section of the individual hairs, at the skin surface or at a predetermined distance above the skin surface.

Pursuant to another feature of the present invention, a marker film is applied to a light-treated skin surface to indicate that electromagnetic radiation has been applied to the skin surface. The marker film may include a visually detectable pigment, for instance, zinc oxide, titanium dioxide, or a tinted transparent wash or dye. Alternatively, the marker film may be a visually undetectable, exemplarily micronized or microfine zinc oxide. In that case, the light application device is provided with a sensor that detects the marker film and disables or blocks light application to any skin surface already treated with an effective amount of light.

The marker film is preferably applied by the same device that generates the light and directs the light to a skin surface. In that case, the device is provided with a reservoir of the marker composition and an applicator such as a roller, nozzle, or atomizer.

Where several passes of light application are to be made to the skin surface, each may be marked by an indicator composition of a respective tint or color. The marker compositions should be both biocompatible and water soluble for easy removal.

A hair treatment device in accordance with another feature of the present invention the present invention comprises a hand-holdable casing, a generator of electromagnetic radiation mounted to the casing, and at least one optical element mounted to the casing so as to direct electromagnetic radiation produced by the generator in a direction substantially parallel to a skin surface, to impinge on hair fibers protruding from the skin surface. The optical element may take the form of a partially reflective and partially transmissive mirror.

A light treatment device comprises, in accordance with a further feature of the present invention, a hand-holdable casing, and an applicator interface attached to the casing, the interface including a liquid-filled chamber having a flexible skin-contacting surface or panel. A generator of electromagnetic radiation is mounted to the casing, while at least one optical element mounted to the casing directs light from the generator through the liquid in the chamber towards a skin surface in contact with the flexible skin-contacting surface or panel. Preferably, the flexible skin-contacting surface or panel is transparent to the light from the generator.

A light treatment method in accordance with an additional feature of the present invention comprises generating light of a selected spectral composition, dividing the light into at least two bundles of light rays of substantially mutually exclusive wavelength ranges, and directing at least one of the bundles of light rays towards a skin surface.

Where the one bundle of light rays is directed into the skin surface, the other bundle may be directed substantially parallel to the skin surface to impinge on hairs protruding from the skin surface. The one bundle may include (visible) wavelengths in a range below approximately 750 nm, while the other bundle includes (infrared) wavelengths in a range above approximately 750 nm. Goggles for wear during light treatment in accordance with this feature of the invention may be provided with lenses substantially opaque to light rays of the infrared bundle and at most partially transparent to a selected band of light rays of the visible bundle, as discussed above.

A hair treatment method comprises, in accordance with yet another feature of the present invention, generating light of a selected spectral composition, applying a dye to hair along a skin surface, and thereafter directing the generated light towards the dyed hair along the skin surface. This method is of particular for the removal of hair that is white or very light colored. It should be understood that the present methodology may be used in professional settings, in spas or salons, by professional cosmetic service providers. Higher energies may be used in such settings. Licensed medical professionals in medical offices may use even higher energies and more complex settings.

DETAILED DESCRIPTION OF THE PREFERRED EMBODIMENTS

As described herein, a method for treating skin as a prophylactic to Xray or ultraviolet radiation damage includes the application, to a skin surface, of electromagnetic energy in the visible and/or infrared portions of the electromagnetic spectrum. The applied energy is alternatively referred to herein as "electromagnetic radiation" or "light." The skin surface is generally in a preclinical condition, that is, there is either no Xray or ultraviolet radiation damage or it is so slight as to be undetectable upon visual inspection.

Figure 1:
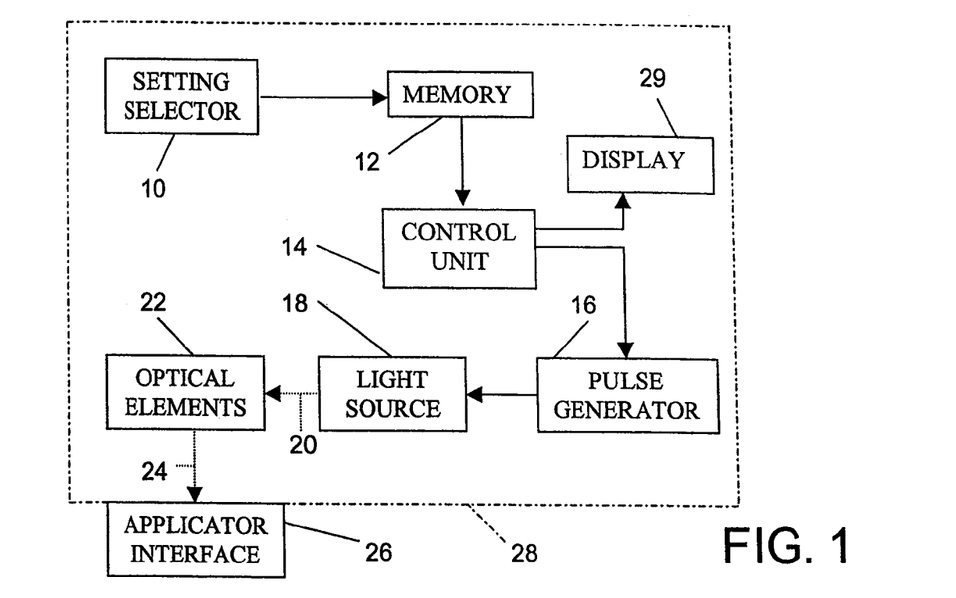
FIG. 1 is a block diagram of a light-pulse generating device for use in a method in accordance with the present invention.

As depicted in FIG. 1, a device for generating light pulses for application to a skin surface in a skin treatment process includes a manually operable setting selector 10 connected at an output to a memory 12 in turn connected at an output to a control unit 14. Memory 12 stores pre-established combinations of light pulse parameters including pulse width or duration, inter-pulse interval or delay time, pulse number, light intensity, and total treatment energy. Control unit 14 may be a microprocessor or a special logic circuit connected to a pulse generator 16 for inducing the generator to produce a sequence of electrical control pulses fed to a source 18 of incoherent light energy. Source 18 produces light with a spectral distribution including wavelengths between 400 nm and 1200 nm. Control unit 14 may be connected directly to source 18 where the source incorporates means for varying pulse parameters pursuant to encoded instructions.

Light source 18 (as well as the entire light pulse applicator) may take any known form such as those disclosed in U.S. Pat. No. 6,280,438 and U.S. Pat. No. 5,885,273. Thus, light source 18 may be a Xenon flashlamp.

Light 20 generated by source 18 is directed through an array of optical elements 22 that may include one or more reflectors, lenses, and filters (not separately shown). Where an adjustable filter is included, control unit 14 may be connected to the filter for operatively modifying the action thereof. For instance, in the case of an adjustable neutral density filter, control unit 14 may induce a change in the filter density to control the intensity, and therefore the power, of the light applied to a selected skin surface.

In the case of multiple wavelengths of light being produced, an adjustable filter may be included in the optical elements 22 and/or the applicator interface 26. These filters can block undesired wavelengths and allow desired wavelengths to pass. Low end filters that block lower or shorter wavelengths, high end filters that block higher or longer wavelengths or band pass filters that block some high or some low end wavelengths may be utilized.

Figure 2:
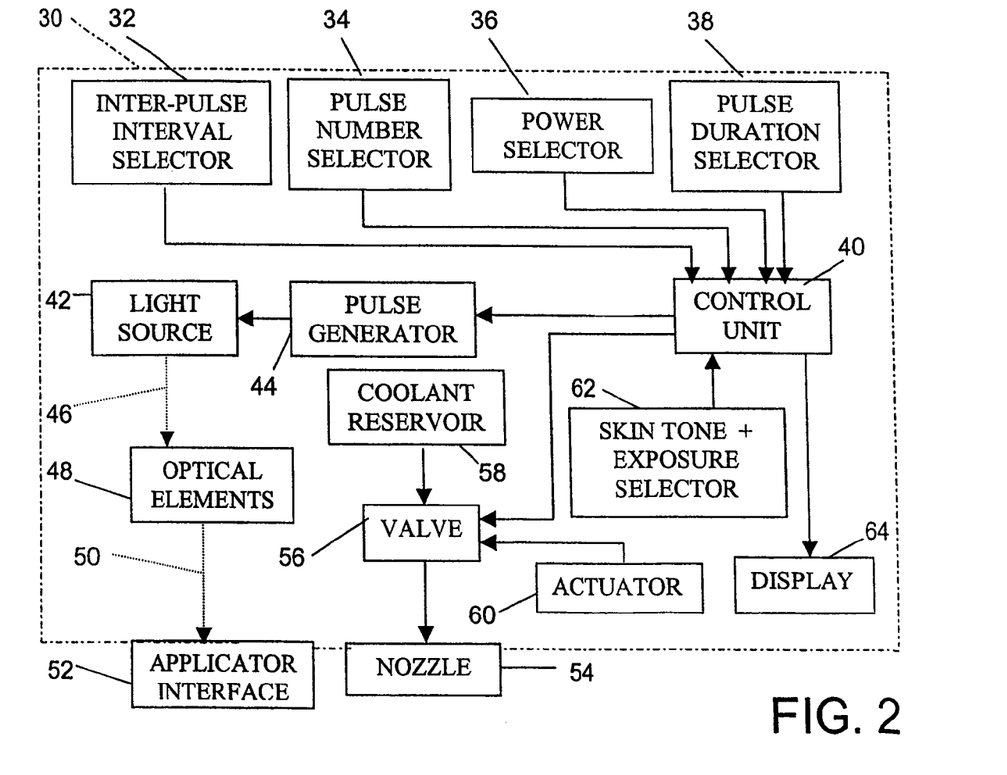
FIG. 2 is a block diagram of another light-pulse generating device for use in a method in accordance with the present invention.

Light 24 leaving the optical array 22 is delivered or applied to a skin surface via an applicator or interface element 26 exemplarily taking the form of a crystal. U.S. Pat. No. 6,280,438 and U.S. Pat. No. 5,885,273 disclose kinds of applicators or interfaces utilizable in the device of FIG. 1 (or 2). Applicator or interface element 26 may function in part to cool the skin surface prior to, during, and/or after a light application procedure. Cooling may be accomplished by using a crystal-type applicator or interface 26, with or without a layer of gel, as described in U.S. Pat. No. 6,280,438 and U.S. Pat. No. 5,885,273.

The elements of FIG. 1 are encased in or mounted to a housing 28 of a size and configuration enabling the pulse generation device to be hand held and easily manipulated for purposes of optically treating different skin surfaces of the individual user.

The device of FIG. 1 is preprogrammed to produce light pulses in any of several settings, each setting being defined by a respective combination of particular operational parameters including pulse duration, inter-pulse interval, pulse number, and intensity or total energy. For instance, the device may have a plurality of settings, for instance, high, medium, and low, which vary in the number of applied pulses (e.g., 3, 2, 1), the pulse duration (9 msec, 7 msec, 5 msec), the inter-pulse interval (250 msec, 300 msec, 350 msec), and/or the total energy applied (35 J/cm$^2$, 20 J/cm$^2$, 10 J/cm$^2$). Usually, it is preferable to use the lowest setting which accomplishes the desired result. Generally, dark skin is more effective at light absorption that light skin and should be treated with lower settings (e.g., less overall energy) than light skin.

Setting selector 10 has a plurality of discrete settings differentiated at least on the basis of skin tone. Different skin settings may include, for instance, dark skin, medium-tone skin, and light skin, or black, coffee, brown, tan, cream, and white. Setting selector 10 may also include a separate group of exposure settings for users to identify the degree of sun exposure they have or expect to have. Exposure settings may include, for example, singular, occasional, frequent, and constant.

Control unit 14 may be connected to an LCD or other readable display 29 for communicating to the user a recommended treatment schedule or program in response to the entries made by the user via selector 10. Depending on the user input, the read-out on display 29 may indicate such schedules as twice daily, once a day, once every other day, weekly, once on each of 3 days before sun exposure, just before exposure to sun, immediately before and after exposure to sun. The operational parameters, including pulse duration, inter-pulse interval, pulse number, and intensity or total energy, are selected by control unit 14 to conform to the recommended treatment schedule.

A more advanced or complex device is illustrated in FIG. 2. This device includes a housing 30 having manually actuatable input elements 32, 34, 36, and 38, such as rotary knobs or a solid-state touch screen, which enable a user to individually select multiple operating parameters. Input elements or selectors 32, 34, 36, and 38 are an inter-pulse interval selector, a pulse number selector, a power or energy selector, and a pulse duration selection, respectively. Another selector (not shown) could be for intensity adjustment, while a further selector may be provided for adjusting a light source 42 or a filter in optical elements 48 and/or an applicator 52 for modifying the wavelength band delivered to the target skin surface. Selectors 32, 34, 36, and 38 are operatively tied to a control unit 40 such as a microprocessor or hard-wired log circuit. Control unit 40 regulates the operation of light source 42 such as a conventional flashlamp, either directly or indirectly via a pulse generator 44. Light 46 from source 42 is transmitted along a path through optical elements 48 optionally including one or more reflectors, lenses, and filters (not separately shown). Light 50 at an output of the optical array 48 is applied to a skin surface via applicator or interface element 52. Applicator or interface element 52 may take the form of a crystal block, a flexible plastic element, and/or a transparent or translucent pouch filled with a transparent or translucent fluid such as a gel or a liquid. In the case of the flexible element or the fluid-filled pouch, applicator or interface element 52 conforms at least partially to the changing topography of the skin surface under treatment, thereby facilitating the retention of gel between the applicator or interface 52 and the skin surface. This result decreases the likelihood of overexposed or burned skin and generally provides a more uniform application of light with a uniformity of cooling. Safety is enhanced, while the outcomes to successive procedures become increasingly standardized.

Where applicator 52 (or 26) includes a gel-filled pouch, the pouch (52) may be provided with perforations on a skin-contacting surface for exuding the gel for cooling purposes. Alternatively, as shown in FIG. 2, the light pulse device may be provided with a fluid dispenser such as a spray nozzle 54 connected to a valve 56 downstream of a pressurized coolant reservoir 58. In response to an operation of a manual actuator 60 or in response to signals from control unit 40, valve 56 enables a flow of coolant from reservoir 58 to nozzle 54 for application to a selected skin surface. In the event that applicator or interface element 52 is a bag or pouch, reservoir 58 and valve 56 may be connected to the applicator or interface element for supplying a gel or fluid coolant thereto.

In one embodiment of the device of FIG. 2, suitable for professional but not home use, inter-pulse interval selector 32 provides for intervals in a range from 1 msec and 2 seconds, whereas pulse number selector 34 is enabled for pulse sequences of one to ten pulses. In addition, power selector 36 permits treatment energies between 0.01 Joule per square centimeter of skin surface and 200 Joules per square centimeter, while pulse duration selector 38 enables pulses of 1 msec to 2 seconds in length. Total pulse sequence duration, from the beginning of the first pulse to the termination of the final pulse, ranges from 1 msec to 38 seconds. The various pulse sequence parameters may be selectable from sets of discrete values or, alternatively, from continuous ranges.

In the device of FIG. 2, the various parameters are typically not completely independent inasmuch as the total energy selected will function as a constraint on the ranges available for the other parameters, that is, the total energy selected will serve to regulate or circumscribe the ranges available to the user for the other pulse sequence parameters. Where the device of FIG. 2 has no intensity adjustment capability, a selection of the total energy and the pulse duration may determine the number of pulses. Similarly, a selection of the total energy and the number of pulses may determine the pulse duration. If the intensity is an adjustable parameter, once the total energy has been chosen, the user will be able to select the magnitudes of two of the three parameters, pulse duration, intensity and number of pulses. The inter-pulse interval is related to the rate at which radiant energy is applied to a skin surface and may accordingly be subjected to some programmed control. Longer pulse durations and/or delays will deliver energy at a slower rate (total energy is distributed over longer time) and therefore be safer to use with higher energy levels. Preferably, the total energy is always a selectable parameter and is best selected prior to the setting of the other parameters. However, the device of FIG. 2 may be preprogrammed to limit the rate at which radiant energy is applied to a skin surface, which will force restrictions on the user's ability to select pulse parameter values.

In an alternative embodiment of the device of FIG. 2, suitable for home use, inter-pulse interval selector 32 enables a selection of intervals ranging from 200 msec to 2 seconds, while power selector 36 enables treatment energies between 1

J/cm² and 40 J/cm². Preferably, the pulse duration and the number of pulses available for selection are restricted so as to prevent the user from delivering energy at too high a rate. If the user selects a large pulse number, the pulse duration is necessarily short, whereas a small number of pulses forces a longer pulse duration in order to achieve the selected total energy. Delivering the same energy over long pulse periods is safer. It is preferable to use a largest possible total pulse duration, assuming that none of the individual pulse durations are shorter than a critical threshold level. Pulse number selector 34 may therefore enable a selection of three to ten pulses per pulse sequence, while pulse duration selector 38 enables a selection of pulses lasting 1 msec to 10 msec. The various pulse sequence parameters may be selectable from sets of discrete values or, alternatively, from continuous ranges.

A person uses the device of FIG. 1 or 2 to apply pulses of light to a skin surface for purposes of effectively preventing or repairing damage done by ultraviolet light to the cells of the skin and/or below the surface of the skin. The absorption of the light pulses by melanin and other chromophores in the user's epidermal, dermal and subdermal tissues is believed in part to promote the production of chemicals that reduce the incidence of Xray or ultraviolet radiation damage and inhibit the growth of cancerous cells. In addition, the light energy may increase skin temperature slightly, through absorption and/or light scattering, for purposes of advancing tissue regenerative processes.

As further illustrated in FIG. 2, the light pulse applicator of that drawing figure may include an additional selector 62 for enabling the user to load a skin tone value and an expected sun exposure level into control unit 40. Setting selector 62 may take the form of a knob, a keypad, or manual switch enabling the user to enter a skin tone value from a plurality of possible values. The possible selections may be qualitative descriptions: black, coffee, brown, tan, cream, white, etc. Alternatively, the possible skin tone selections may be quantitative where the integer 1 corresponds to the whitest skin tone while the numeral 10 represents the darkest possible skin tone.

Setting selector 62 may also include a separate group of exposure settings for users to identify the degree of sun exposure they have or expect to have. Exposure settings may include qualitative descriptors: singular, occasional, frequent, and constant. Alternatively, the possible exposure level selections may be any rational number along a continuum between 0 and 10, where the lower boundary represents no sun exposure and the higher limit corresponds to continuous sun exposure.

Other possible input into control unit 40 via selector 62 may encode the climate and season. For this parameter, a low value such as 0 might represent winter in a polar region while 10 or 100 represents summer in an equatorial region.

Control unit 40 may be connected to an LCD or other readable display 64 for prompting the user as to information to be input via selectors 32, 34, 36, 38 and 62 and for communicating to the user a recommended treatment schedule or program in response to the entries made by the user via selector 62. Control unit 40 may also use display 64 to alert the user as to impermissible parameter combinations. Depending on the skin tone and sun exposure input received via selector 62, control unit 40 may reject certain light parameter selections made by the user. The reason for rejecting the user's selection of light pulse parameters may be communicated to the user via display 64. Ranges of permissible values may be displayed to facilitate the user's selection. The permissible ranges for outstanding parameters will vary depending on the user's prior selections as discussed above.

In response to user input of skin tone and sun exposure levels, control unit 40 may indicate on display 29 a plurality of possible light treatment schedules. The user may actuate selector 62 to choose a preferred treatment schedule. This choice is preferably made prior to the selection of one or more light pulse parameters via selectors 32, 34, 36, and 38. The available ranges of the remaining parameters will be limited in accordance with the user's selection of treatment schedule.

Generally, light treatment schedules are determined automatically in accordance with a user's input to the light treatment device. To the extent that the user is allowed leeway in selecting individual pulse parameters, the device may impose limitations in accordance with the selected skin tone and sun exposure characteristics, as well as one or more pulse parameters initially selected by the user.

The devices of FIGS. 1 and 2 may be used alternatively in the temporary removal of hair and/or the retardation of hair growth. The light treatment may be undertaken as an "aftershave" after the visible or protruding hair has been removed by a conventional process such as by razor or shaver.

The devices of FIGS. 1 and 2 are optionally provided with photocells and light-emitting LEDs (none illustrated) for purposes of measuring skin tone. The light pulses parameters may then be automatically selected in accordance with the measured skin tone. The LEDs and photocells are connected to the respective control unit 14, 40 for taking measurements in response to signals from that unit.

In another optional modification, the devices of FIGS. 1 and 2 may be provided with infrared sensors (not shown) for generally sensing a degree of sun exposure. This option is useful principally for light-pulse application immediately after sun exposure. The infrared sensor is operatively connected to the respective control unit 14, 40 to inform unit's selection of pulse parameters. Where there is a marked degree of sun exposure (resulting in a high skin temperature and a greater-than-usual emission of infrared radiation), control unit 14, 40 may select pulse parameters for a maximum possible energy application. For a single session, the treatment may have the longest possible duration (30-40 seconds). Alternatively, particularly with the device of FIG. 2, control unit 40 may recommend to the user a series of treatment sessions spread out over several days.

In yet another optional modification, the user of a skin treatment device as described with reference to FIG. 1 or 2 may be provided with a UV sensor (not illustrated) for sensing the degree of sun exposure. If the sensor is on the light treatment device, the sensor may be connected to control unit 14, 40. The sensor and the control unit 14, 40 may cooperate to measure a total amount of UV exposure. The control unit is programmed to select light treatment parameters and possibly a treatment schedule in accordance with the detected instantaneous or cumulative amount of UV radiation. The light treatment may be during or after the UV exposure.

Figure 3:
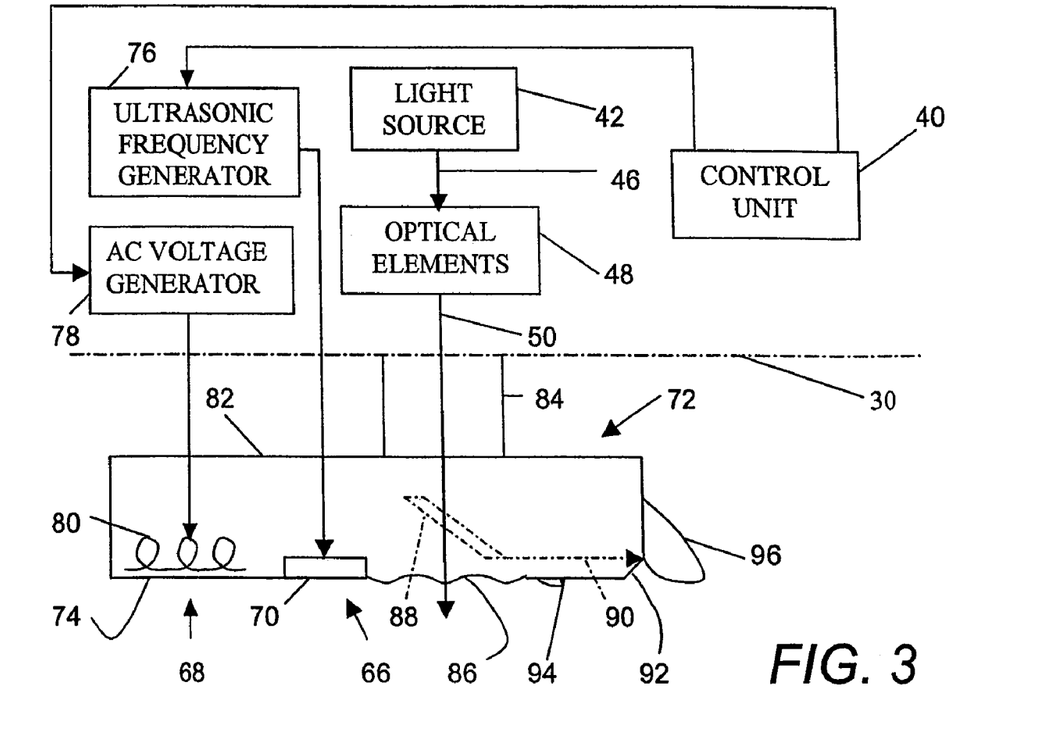
FIG. 3 is a schematic diagram of possible modifications to the light-pulse generating device of FIG. 2.

As depicted in FIG. 3, the light treatment devices of FIGS. 1 and 2 may incorporate a generator 66 of ultrasonic vibrations and/or an electromagnet 68 for enabling the application of ultrasound energy or a magnetic field (preferably oscillating) to a skin surface before, during or after the application of light energy. Permissible and recommended variations in the relevant parameters are well known in the skin treatment arts. In the case of ultrasound energy, one or more piezoelectric crystals 70 are disposed in or in contact with an applicator interface 72, e.g., a fluid-filled member having a flexible panel 74 for contacting and conforming to the skin surface.

A waveform generator 76 transmits an ultrasonic-frequency electrical signal to the piezoelectric crystal(s) 70 for producing ultrasonic vibrations in skin tissues. An AC voltage generator 78 is operatively connected to an electromagnetic coil 80 for generating an alternating magnetic field in the skin tissues.

The applicator interface 72 of FIG. 3 includes an enlarged contact member or head 82 connected to the housing 28, 30 by a stem 84. Head 82 and optionally stem 84 are filled with a coolant fluid such as water or a gel. Prior to the use of the light-generating instrument, head 82 and optionally stem 84 may be stored in a refrigeration unit for purposes of reducing the temperature the water or gel. In that event, head 82 or stem 84 is provided with a connector (not shown) for detachably coupling the head or the stem to housing 28, 30. The connector includes electrical contacts (not shown) for the transmission of ultrasonic electrical waves from frequency generator 76 and another signal from AC voltage generator 78. In an alternative, more expensive embodiment of a light generating apparatus, the fluid in interface 72 may be circulated from a heat exchange unit (not shown) by a pump (not shown).

Applicator interface 72 has an opaque outer surface (not separately designated) except along an area 86 of skin-contacting panel 74 opposite stem 84. Light 50 at an output of the optical array 48 is transmitted through stem 84, head 82, and transparent area 86.

As illustrated in FIG. 3, piezoelectric crystals 70 and coil 80 may be disposed inside head 82. Where the fluid is electrically conductive, crystals 70 and coil 80 are provided with appropriate electrical insulation such as a coating of a thermoplastic resin material. Alternatively, crystals 70 and coil 80 may be disposed inside housing 28 or 30. In that case, crystals 70 are in mechanical contact with stem 84 so as to enable the transmission of ultrasonic pressure waves through stem 84 and head 82 to panel 74. Electromagnetic coil 80 is of such as size that the magnetic field generated inside the dermal tissues is sufficiently large to effectively treat the skin tissues, in conjunction with the light treatment and optionally ultrasound.

As depicted in FIG. 3, head 82 is further provided with optics (e.g., a partially silvered mirror 88) for transmitting light 90 in a direction parallel to a skin surface. The light exits head 82 at a window 92 provided along a leading edge of the head for purposes of applying the light to hair protruding from the skin surface. The light 90 singes the hair which is then broken off by a bumper element 94 protruding slightly from a lower surface of panel 74. The removal of the hair enhances the effectiveness of the light penetration into the dermal tissues. A shield 96 may extend from the leading end of head 82 to block the escape of light 90 from a hair-treatment space immediately in advance of window 92.

Mirror 88 is tilted at an approximately 45° angle to the direction of transmission of light 50, i.e., at an approximately 45° angle to a perpendicular or normal to the skin surface. In a variation on the hair removal feature implemented via mirror 88, the mirror is tilted at a 90° angle to the orientation shown in FIG. 3, for reflecting, in the direction of transmission of light 90 (generally parallel to the skin surface), that portion of light beam 50 that has been reflected from the target skin surface. Thus, reflected light is used to shave hair, the singing and breaking of the hairs occurring generally at the point of emergence thereof from the skin surface. This embodiment of the device of FIG. 3 tends to conserve energy relative to the illustrated embodiment. Thus, the light treatment device can be made with a less powerful light source, reducing the cost of the device.

The embodiment of FIG. 3 may be modified to produce a light treatment device solely for hair removal at the skin surface alone. In that case, mirror 88 may be completely reflective so as to direct all the light of "vertical" beam 50 to form "horizontal" beam 90.

Figure 4:
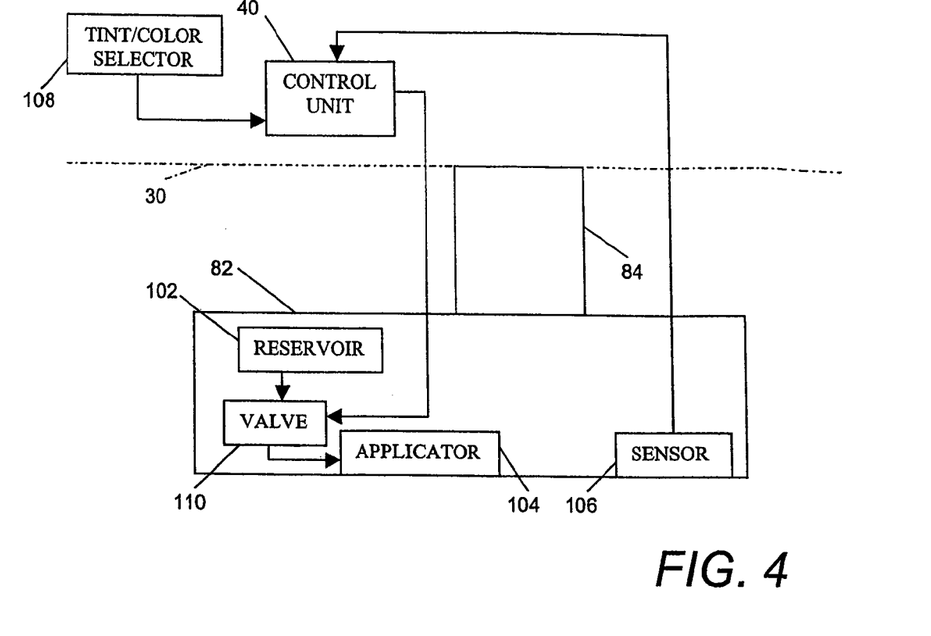
FIG. 4 is a schematic diagram of possible additional or alternative modifications to the light-pulse generating device of FIG. 2.

As depicted in FIG. 4, the light treatment devices of FIGS. 1, 2 and 3 may incorporate a reservoir 102 of a composition to be applied as a marker film to a light-treated skin surface to indicate that electromagnetic radiation has been applied to the skin surface. The marker film composition in reservoir 102 may include a visually detectable pigment, for instance, zinc oxide, titanium dioxide, or a tinted transparent wash or dye. Where multiple passes are to be made to a skin surface, the first and other non-final passes may leave a transparent or partially transparent film, while the final pass deposits an opaque coating (e.g., zinc oxide or titanium dioxide) that is reflective so as to protect the skin against further inadvertent light exposure. The initial film deposits may be partially reflective to provide some measure of protection against inadvertent overexposure. Alternatively, the marker film composition in reservoir 102 may be a visually undetectable substance, such as micronized or microfine zinc oxide. In any case, the marker composition(s) in reservoir 102 are preferably both biocompatible and water soluble for easy removal.

As further depicted in FIG. 4, the light treatment devices of FIGS. 1, 2 and 3 may also incorporate an applicator 104 communicating with reservoir 102 and disposable in proximity to a skin surface applying metered amounts of the marker film composition to the skin surface upon an administration of light to the skin surface pursuant to the disclosure hereinabove. Applicator 104 exemplarily takes the form of a roller, a brush, a nozzle, or an atomizer.

Where the marker film composition in reservoir 102 is a visually undetectable substance, the light application device is provided with a sensor 106 that detects whether the marker film composition is present on a skin surface. In the event sensor 106 detects the presence of the marker film composition, the sensor disables or blocks light application to the respective skin surface. Sensor 106 may be connected to microprocessor or control unit 14 or 40 for inducing that unit to interrupt, or terminate the generation of light by generator 16, 44, or 66.

Where a light treatment procedure involves several passes along a target skin surface, each pass may be marked by an indicator composition of a respective tint or color. In that case, reservoir 102 includes a plurality of sub-reservoirs each containing a composition of a respective tint or color. A button, knob or other input element 108 may be operatively connected to the microprocessor or control unit 14 or 40 for selecting the color or tint of the marker film composition to be applied to the skin. Microprocessor or control unit 14, 40 may implement the color or tint selection by operating a valve 110 disposed between reservoir 102 and applicator 104.

Where the marker film composition in reservoir 102 includes a dye that is absorbed into hair, the applicator 104 may be used to apply a dye to light colored or white hair prior to an application of light to the hair. The dye is applied to the hair along a selected skin surface, and thereafter light is directed towards the dyed hair. This method is of particular for the removal of hair that is white or very light colored. A button or other input element (not shown) may be provided for disabling the light application during the application of the dye to the hair.

Figure 5:
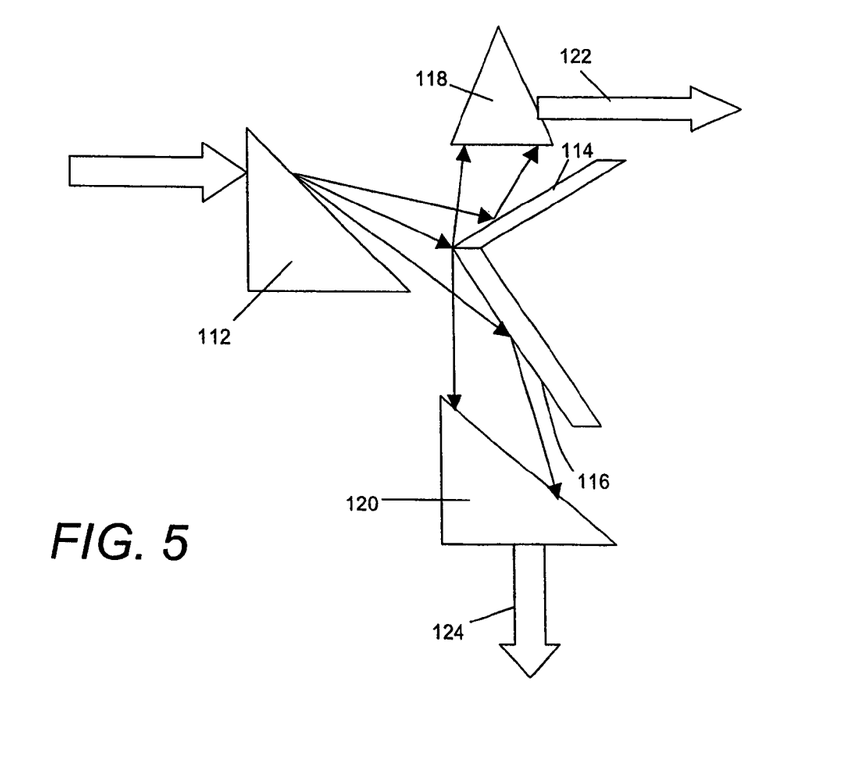
FIG. 5 is a schematic diagram showing optics that may be incorporated into a light treatment device in accordance with the present invention.

As shown in FIG. 5, optical elements 22 or 48 of the light treatment devices of FIGS. 1, 2 and 3 may incorporate a primary prism 112, two mirrored surfaces 114 and 116, and a pair of secondary prisms 118 and 120 for splitting light from source 18 or 42 into at least two bundles 122 and 124 of light rays of substantially mutually exclusive wavelength ranges.

At least one of the bundles of light rays 122 is directed towards a skin surface. The other bundle 124 may be directed substantially parallel to the skin surface to impinge on hairs protruding from the skin surface, as discussed above with reference to FIG. 3. Bundles 122 and 124 each typically include visible wavelengths.

The user of the light treatment device of FIG. 5 may be provided with goggles (not shown) having lenses that are substantially opaque to light rays of bundle 122 and at most only partially transparent to a selected band of light rays of bundle 124. The goggles are effectively opaque to wavelengths outside of the selected band. If the goggles are completely transparent to this narrow wavelength band, the band is filtered out of bundle 124. An indicator light such as an LED (not shown) may be provided that emits light in the narrow band to provide a signal to the user that dangerous radiation is being produced. Alternatively, the goggles may be at most partially transparent to the narrow wavelength band. In this case, the goggles transmit enough light of the narrow band to enable visual detection but not enough to damage the eye.

It is possible to generate a "vertical" bundle of essentially only visible wavelengths (shorter than about 750 nm) and a "horizontal" bundle of only infrared wavelengths (longer than about 750 nm). This kind of wavelength distribution over the bundles may be implemented by having separate radiation generators and at least partially separate transmission paths. Alternatively, if a single generator produces both visible and infrared radiation, optics may be provided for splitting out the visible wavelengths from the infrared wavelengths.

In determining optimal settings with the device of FIG. 2, a user should choose initial parameter values which in combination result in the application of small amounts of energy. Thus, where one or more selected pulse parameters tend to produce higher treatment energies, other pulse parameters should be selected that that tend to produce lower treatment energies.

Where all the pulse parameters are independently adjustable, lower treatment energies will generally result from settings involving few pulses (say, 1-3 instead of 8-10 pulses), long inter-pulse intervals (300 msec or more), short pulse durations (20 msec or less), low light intensity (if selectable, for example, via an adjustable neutral density filter), and low total energies (less than 40 Joules per square centimeter of skin surface). If a given setting proves to be ineffective in improving skin appearance after sun exposure, the user might adjust selector 32 or 38 to decrease the inter-pulse interval or decrease the pulse length, thereby effectively increasing the power or rate at which the radiant energy is delivered to the target skin surface. Alternatively or additionally, the user might increase the number of pulses via selector 34 or increase the applied energy via selector 36. These adjustments will result in an increase in the rate of applied energy if the total time of the pulse sequence is limited. If the light intensity is separately adjustable, one may increase the power or rate of energy delivery by simply selecting a higher intensity value.

Where the various pulse parameters are not independently selectable, for instance, where the total energy applied is a controlling factor, adjustments made in the parameters for purposes of incrementally enhancing the skin treatment effectiveness of the device of FIG. 2 will be different from the case of completely independent parameter values. For instance, once the total applied energy and total pulse sequence time have been selected, decreasing the number of pulses will require an increase in pulse length and/or an increase in pulse intensity in order to deliver the same amount of total energy in the fixed time. These changes will increase the effectiveness of the light application inasmuch as the rate of energy delivery is increased. In contrast, once the total applied energy and total pulse sequence time have been selected, increasing the pulse duration will decrease the instantaneous rate at which energy is applied to the target skin surface by decreasing the light intensity.

Because different skin areas have different skin pigmentation, different vascularization, etc., different pulse parameter settings are recommended for different skin areas. For example, different settings will be necessary for the lower surfaces of the arms, the backs of the knees, and the upper surfaces of the feet in order to optimize results.

The present skin treatment method contemplates the application to a selected skin surface of a pulse sequence having a predetermined number of pulses of light of a predetermined electromagnetic spectrum, a predetermined duration, a predetermined inter-pulse interval, and a predetermined total energy. These pulse sequence parameters are determined in part by the design of the light-generating device used and in part by the selections as to skin tone and, optionally, sun exposure level made by the user.

The light of the pulses is generally incoherent and the spectrum includes wavelengths between about 400 nm and 1200 nm. However, single wavelengths of laser or coherent light may be delivered at one time, when desired. Higher wavelengths are used for darker skin and/or for deeper penetration into dermal tissues.

The light applied to a skin surface by the devices of FIGS. 1 and 2 includes at least one wavelength absorbable by an endogenous chromophore in a person's skin. The endogenous chromophore may be a form of melanin. Alternatively or additionally, the endogenous chromophore is hemoglobin. In a more advanced embodiment the light application device may include a setting or control (not shown) for selecting a spectrum or range of wavelengths appropriate to the user's skin color. In any event, the devices of FIGS. 1 and 2 are generally used without the application of an exogenous chromophore to a target skin surface for light absorption purposes. However, it is possible for an individual to apply an exogenous chromophore such as porphyrin that is absorbed by the skin cells. Of course, the user should vary the light treatment to accord with the resulting light absorption.

In other embodiments of a light generation and application device for hair treatment, one or more of the pulse parameters may vary during a single treatment session. For instance, the inter-pulse interval or the pulse duration may increase or decrease from the beginning of a pulse sequence to the end of the pulse sequence. The resulting instantaneous rate of energy application may therefore vary during the pulse sequence.

Listed below are a number of exemplary settings or combinations of operational parameters particularly suitable for home-use and attainable with either the device of FIG. 1 having pre-established settings or parameter combinations or the device of FIG. 2 where the various pulse sequence parameters may be individually adjusted independently of the other parameters. In these examples, the total times of the pulse sequences are determined by the selected numbers of pulses, the selected pulse durations and the selected inter-pulse intervals. The light intensity may be automatically adjusted by the light generating device if necessary to ensure consistency among the listed parameter settings.

Home Use Example 1

In a preferred setting or combination of operational parameters suitable for home use, an incoherent light applicator device for skin treatment generates pulses with a pulse number of two, a pulse duration of 7 msec, an inter-pulse interval of 300 msec, a total pulse energy of 20 J/cm², and a spectral distribution of a commercially available flashlamp, including wavelengths between 500 and 1200 nm.

Home Use Example 2

A slightly higher setting or combination of operational parameters for an incoherent light applicator device suitable for home use involves a pulse sequence with a pulse number of two, a pulse duration of 7 msec, an inter-pulse interval of 250 msec, a total pulse energy of 20 J/cm², and a spectral distribution of a commercially available flashlamp, including wavelengths between 500 and 1200 nm. Although the total amount of energy is the same as in the first example, the shorter interpulse interval means that the rate of energy transmission to the target skin surface is higher.

Home Use Example 3

A higher setting or combination of operational parameters for an incoherent light applicator device involves pulses with a pulse number of two, a pulse duration of 5 msec, an inter-pulse interval of 250 msec, a total pulse energy of 25 J/cm², and a spectral distribution of a commercially available flashlamp, including wavelengths between 500 and 1200 nm. In this example, not only is the total energy larger than in the second example, but the rate of energy application is higher owing to the shorter pulse duration.

Home Use Example 4

An even higher setting or combination of operational parameters for an incoherent light applicator device involves pulses with a pulse number of two, a pulse duration of 5 msec, an inter-pulse interval of 210 msec, a total pulse energy of 37 J/cm², and a spectral distribution of a commercially available flashlamp, including wavelengths between 500 and 1200 nm. The pulse sequence of this example delivers radiant energy at a higher rate than in the third example because of the shorter inter-pulse interval and the slightly higher energy delivered per pulse.

Home Use Example 5

In a low setting or combination of operational parameters, an incoherent light applicator device produces pulses with a pulse number of two, a pulse duration of 5 msec, an inter-pulse interval of 350 msec, a total pulse energy of 15 J/cm², and a spectral distribution of a commercially available flashlamp, including wavelengths between 500 and 1200 nm. The pulse sequence of this example delivers a small amount of energy, at a low rate (e.g., long inter-pulse interval).

Home Use Example 6

A slightly higher setting or combination of operational parameters for an incoherent light applicator device involves pulses with a pulse number of two, a pulse duration of 5 msec, an inter-pulse interval of 300 msec, a total pulse energy of 20 J/cm², and a spectral distribution of a commercially available flashlamp, including wavelengths between 500 and 1200 nm.

Home Use Example 7

A lower setting or combination of operational parameters for an incoherent light applicator device involves pulses with a pulse number of three, a pulse duration of 5 msec, an inter-pulse interval of 300 msec, a total pulse energy of 20 J/cm², and a spectral distribution of a commercially available flashlamp, including wavelengths between 500 and 1200 nm.

Home Use Example 8

Another setting or combination of operational parameters for an incoherent light applicator device involves pulses with a pulse number of two, a pulse duration of 7 msec, an inter-pulse interval of 250 msec, a total pulse energy of 20 J/cm², and a spectral distribution of a commercially available flashlamp, including wavelengths between 500 and 1200 nm.

The devices of FIGS. 1 and 2 may be provided with a band-pass filter for limiting the spectral distribution of the generated light pulses to wavelengths in a given band, for instance, between 700 nm and 900 nm. Alternatively, a low-pass filter may be used for transmitting to a skin surface only wavelengths less than a predetermined maximum, such as 900 nm, 750 nm, or 550 nm. The lower the wavelength the less likely the light will penetrate deeply and damage cellular and histological elements as deep as the bulb parts of the hair follicles. Shorter wavelengths, for instance, below 550 nm are useful for limiting the depth of penetration.

Depth of penetration may also be limited by using lower light intensities. Neutral density or "gray" filters may be used to reduce the intensity of the light applied to the selected skin surfaces.

Listed below are a number of exemplary settings or combinations of operational parameters particularly suitable for professional devices. In these examples, the selected numbers of pulses, the selected pulse durations and the selected inter-pulse intervals determine the total times of the pulse sequences. The light-generating device, if necessary to ensure consistency among the listed parameter settings, may automatically adjust the light intensity.

Professional Use Example 1

In a setting or combination of operational parameters suitable for professional use, an incoherent light applicator device for skin treatment generates pulses with a pulse number of two, a pulse duration of 7 msec, an inter-pulse interval of 150 msec, a total pulse energy of 60 J/cm², and a spectral distribution of a commercially available flashlamp, including wavelengths between 500 and 1200 nm.

Professional Use Example 2

A slightly higher setting or combination of operational parameters for an incoherent light applicator device involves pulses with a pulse number of two, a pulse duration of 7 msec, an inter-pulse interval of 100 msec, a total pulse energy of 60 J/cm², and a spectral distribution of a commercially available flashlamp, including wavelengths between 500 and 1200 nm.

Professional Use Example 3

A lower setting or combination of operational parameters for an incoherent light applicator device involves pulses with a pulse number of two, a pulse duration of 9 msec, an inter-pulse interval of 100 msec, a total pulse energy of 60 J/cm², and a spectral distribution of a commercially available flashlamp, including wavelengths between 500 and 1200 nm.

Professional Use Example 4

A higher setting or combination of operational parameters for an incoherent light applicator device involves pulses with a pulse number of two, a pulse duration of 9 msec, an inter-pulse interval of 100 msec, a total pulse energy of 100 J/cm$^2$, and a spectral distribution of a commercially available flashlamp, including wavelengths between 500 and 1200 nm.

Professional Use Example 5

In a relatively low setting or combination of operational parameters for professional use, an incoherent light applicator device produces pulses with a pulse number of two, a pulse duration of 9 msec, an inter-pulse interval of 200 msec, a total pulse energy of 40 J/cm$^2$, and a spectral distribution of a commercially available flashlamp, including wavelengths between 500 and 1200 nm.

Professional Use Example 6

A slightly higher setting or combination of operational parameters for an incoherent light applicator device involves pulses with a pulse number of two, a pulse duration of 5 msec, an inter-pulse interval of 150 msec, a total pulse energy of 40 J/cm$^2$, and a spectral distribution of a commercially available flashlamp, including wavelengths between 500 and 1200 nm.

Professional Use Example 7

Another higher setting or combination of operational parameters for an incoherent light applicator device involves pulses with a pulse number of two, a pulse duration of 5 msec, an inter-pulse interval of 150 msec, a total pulse energy of 50 J/cm$^2$, and a spectral distribution of a commercially available flashlamp, including wavelengths between 500 and 1200 nm.

Professional Use Example 8

A further combination of operational parameters for an incoherent light applicator device involves pulses with a pulse number of two, a pulse duration of about 5.8 msec, an inter-pulse interval of approximately 20 msec, and a total applied energy of between about 20 Joules per square centimeter of said skin surface and about 90 Joules per square centimeter of said skin surface.

Professional Use Example 9

Yet another setting or combination of operational parameters for an incoherent light applicator device involves pulses with a pulse number of one a pulse duration of between about 18 msec and 25 msec, and a total applied energy of between about 20 Joules per square centimeter of said skin surface and about 90 Joules per square centimeter of said skin surface.

An incoherent light applicator device for professional use may also be provided with a band-pass filter for limiting the spectral distribution of the generated light pulses to wavelengths in a given band, for instance, between 700 nm and 900 nm. Again, a low-pass filter may be used for transmitting to a skin surface only wavelengths less than a predetermined maximum, such as 900 nm, 750 nm, or 550 nm.

In the skin treatment method described above with reference to FIGS. 1 and 2, visible and/or infrared light energy is applied to a skin surface for absorption by melanin in the epidermis and hemoglobin in the capillaries and blood vessels of the dermis. The absorption of light (visible and/or infrared) increases the local temperature in the tissues containing the chromophores, particularly the blood vessel cell walls and keratinocytes in the skin. The rise in heat of these structures, and others such as collagen and Langerhans cells, may release factors that stimulate collagen synthesis and/or remodeling.

It is to be noted that the skin treatment method described herein allows for multiple passes over any particular skin surface. The selected light treatment parameters may be the same for each pass or may vary from pass to pass. In addition, the passes may follow immediately after one another or may be spaced by an interval during which, for instance, the light treatment device is used to apply light pulses to another area of the user's skin. An advantage of multiple passes is that the total power applied to a given skin surface may be reduced relative to that needed for accomplishing the desired prophylactic treatment by a single pass. For example, instead of a single pass of 50 Joules/cm$^2$, skin could be effectively treated by two passes of 20 Joules/cm$^2$ apiece. If the number of passes is increased further, the total power may be reduced even more. For instance, twenty passes may require a power no greater than 0.01 Joule/cm$^2$. Multiple passes can be used to treat tanned skin without any undesirable effects. Thus, it is safer to use multiple passes than a single pass. Also, it is more efficient to use multiple passes rather than a single pass. Light application devices for multiple-pass treatments are less expensive and easier to build that devices for single-pass treatments. A scanner may be provided for rapidly implementing a high number of passes without undue exertion by the operator. Where a skin treatment session comprises multiple passes over any particular area of skin, each pass is constituted by one or more light pulses. Where each pass includes multiple pulses in a respective pulse packet, the pulse packets are separated by a period that is great in comparison to the interpulse duration(s) of the pulse packets. This inter-packet period may be anywhere from one-tenth of a second to ten or twenty minutes. Where a hand treatment device as disclosed above with reference to FIGS. 1 and 2 is being used, it is convenient to treat an entire skin surface with a first pulse packet during a first pass and then treat the same skin surface with a second pulse packet during a second pass. Where a light chamber or box is used, the individual need not wait for longer than a few seconds between successive pulse packets, thereby obviating any fatigue or boredom. A prophylactic light treatment as described hereinabove is useful to counteract the deleterious effects of tanning salons as well as of sun exposure, for example, at a beach or swimming pool. In these cases, it is advantageous to the customers of the tanning salon or the users of the beach or pool to provide a light chamber or box where the customers and users may be subjected to a light treatment over large areas of the skin simultaneously. The same chamber that is used for the tanning treatment may be used for prophylactic light treatment. In that case, the visible and/or infrared radiation emitters (bulbs) may be disposed in place of, or in addition to, the tanning radiation sources. The user preferably wears goggles to protect the eyes and may stand or sit in a small enclosure (light chamber or box, not shown) while light energy with appropriate parameters is applied to the entire exposed skin surface. In a light chamber, light may be applied via a contact device, as described specifically hereinabove with reference to FIGS. 1-3, or via a non-contact apparatus, as where the walls of the chamber are provided with diffuse light sources that bathe the individual uniformly in light energy. It is possible also for the light application to be effectuated in a liquid-containing enclosure such as a pool, where a liquid such as an aqueous solution serves in part to conduct light to the skin surfaces of the individual user and to remove excess heat generated in the skin tissues by the absorption or scattering of the light. It is noted in addition that water is a more efficient medium for light transmission than is air. Light may be conveyed to the individual's skin in part via a crystal or pouch-type applicator, as discussed above with reference to FIGS. 1-3, in part via liquid in a pool in which at least a portion of the individual is situated, and/or in part via the ambient air in a light chamber or box, as discussed above.

Although the invention has been described in terms of particular embodiments and applications, one of ordinary skill in the art, in light of this teaching, can generate additional embodiments and modifications without departing from the spirit of or exceeding the scope of the claimed invention. For example, light sources 18 and 42 may take the form of laser sources. In that case, if optical elements 22 and 48 include any filters, those filters are neutral density filters for reducing the intensity of the transmitted radiation. Where light sources 18 and 42 are tunable laser sources, then an additional actuator may be provided for frequency selection purposes. Accordingly, it is to be understood that the drawings and descriptions herein are proffered by way of example to facilitate comprehension of the invention and should not be construed to limit the scope thereof.

What is claimed is:

1. A hair treatment method comprising:
   removing protruding hair fibers from a skin surface by shaving;
   generating a first predetermined number of pulses of light, each pulse having a predetermined electromagnetic spectrum;
   directing said first predetermined number of pulses of light toward said skin surface following said shaving, said pulses having a total energy predetermined to temporarily prevent a growth of hair through said skin surface for a period of time;
   prior to a lapse of said period of time after the directing of said first predetermined number of pulses of light toward said skin surface, and prior to a visible reappearance of hairs on said skin surface, generating a second predetermined number of pulses of light and directing the second predetermined number of pulses of light toward said skin surface to temporarily prevent hair reappearance.

2. The method of claim 1, wherein directing the second predetermined number of pulses of light toward said skin surface to temporarily prevent hair reappearance results in partial damage to one or more hair follicles.

3. A hair treatment method comprising:
   (a) applying a first predetermined number of pulses of light to a skin area that has had protruding hair removed; and
   (b) after step (a), applying a second predetermined number of pulses of light to the skin area before the skin area has had protruding hair regrowth;
   wherein the first predetermined number of pulses of light and the second predetermined number of pulses of light each include:
   (i) a predetermined electromagnetic spectrum, and
   (ii) a predetermined total energy,
   selected to temporarily prevent hair growth through a skin surface.

4. The method of claim 3, wherein the skin area has had protruding hair removed by shaving.

5. A method for temporarily preventing hair growth at a skin surface comprising:
   (a) applying a first predetermined number of pulses of light to a skin area that has had protruding hair removed; and
   (b) applying a second predetermined number of pulses of light to the skin area after step (a) and before the skin area has had visible hair regrowth;
   wherein the first predetermined number of pulses of light and the second predetermined number of pulses of light each include:
   (i) a predetermined electromagnetic spectrum, and
   (ii) a predetermined total energy,
   selected to temporarily prevent hair growth.

6. The method of claim 5, wherein the skin area has had protruding hair removed by shaving.

7. A method of retarding hair growth comprising:
   providing to a skin area a plurality of light applications at an applications frequency, each light application including:
   (a) a plurality of light pulses; and
   (b) a predetermined total energy for the temporary removal of hair;
   wherein the plurality of light applications includes a first light application and a second light application,
   wherein the first light application and the second light application are separated by a time period that is less than the amount of time required for protruding hair growth in the skin area following a hair removal treatment in the skin area and absent any light application following said hair removal treatment.

8. The method of claim 7, wherein the hair removal treatment includes shaving.

9. The method of claim 7, wherein the hair removal treatment includes the first light application.

10. The method of claim 7, wherein the hair removal treatment includes:
    (i) shaving, and
    (ii) the first light application.

11. The method of claim 7, wherein the frequency varies over time.

12. The method of claim 11, wherein the predetermined total energy varies over time.

13. The method of claim 11, wherein the predetermined total energy varies over time due to variation in the number of light pulses in said light applications.

* * * * *